(12) United States Patent
Mercati et al.

(10) Patent No.: US 10,588,933 B2
(45) Date of Patent: Mar. 17, 2020

(54) PLANT-BASED COMPOSITION FOR USE IN THE TREATMENT OF COUGH

(71) Applicant: ABOCA S.P.A. SOCIETÀ AGRICOLA, Sansepolcro (IT)

(72) Inventors: Valentino Mercati, Sansepolcro (IT); Anna Maidecchi, Sansepolcro (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 677 days.

(21) Appl. No.: 15/032,051

(22) PCT Filed: Oct. 27, 2014

(86) PCT No.: PCT/IB2014/065643
§ 371 (c)(1),
(2) Date: Apr. 25, 2016

(87) PCT Pub. No.: WO2015/059683
PCT Pub. Date: Apr. 30, 2015

(65) Prior Publication Data
US 2016/0303179 A1    Oct. 20, 2016

(30) Foreign Application Priority Data
Oct. 25, 2013   (IT) .............................. RM2013A0592

(51) Int. Cl.
| | |
|---|---|
| *A61K 36/53* | (2006.01) |
| *A61K 36/68* | (2006.01) |
| *A61K 36/29* | (2006.01) |
| *A61K 36/899* | (2006.01) |
| *A61K 35/644* | (2015.01) |
| *A61K 36/185* | (2006.01) |
| *A61K 47/36* | (2006.01) |
| *A61K 47/46* | (2006.01) |

(52) U.S. Cl.
CPC .......... *A61K 36/899* (2013.01); *A61K 35/644* (2013.01); *A61K 36/185* (2013.01); *A61K 36/53* (2013.01); *A61K 36/68* (2013.01); *A61K 47/36* (2013.01); *A61K 47/46* (2013.01)

(58) Field of Classification Search
CPC ......... A61K 36/53; A61K 36/68; A61K 36/29
USPC ........................................ 424/738, 747, 777
See application file for complete search history.

(56) References Cited

FOREIGN PATENT DOCUMENTS

DE       42 08 331       10/1992

OTHER PUBLICATIONS

"Tannenblut N Kinder", www.gnpd.com, accession No. 1100967, three pages, Jun. 2009. (Year: 2009).*
"Plants to combat colds and flu" XPO55103963, www.livingmedicine.org/projects/pdf/wh, two pages, Nov. 2010 (Year: 2010).*
Cohn et al. (Pediatrics vol. 130, No. 3, Sep. 2012). (Year: 2012).*
Kadam et al. (Food Chemistry 106 (2008) 1154-1160) (Year: 2008).*
Anonymous "Honey Herb Pastilles" XP002720811, www.gnpd.com, accession No. 1799599, two pages (May 2012).
Snoopmedia Gmbh et al. "Ricola Honig-Kräuter 75 g" XP055103922, das-ist-drin.de/Ricola-Honig-Kraeuter-75-g--420140, four pages (Jan. 2011).
Anonymous "Tannenblut N Kinder" XP002720812, www.gnpd.com, accession No. 1100967, three pages (Jun. 2009).
Anonymous "Propolis Syrup" XP002720813, www.gnpd.com, accession No. 846625, two pages (Jan. 2008).
Anonymous "Lisonatural" XP055103947, www.automedicazione.it/View_Document.aspx?IdDocument=8436, two pages (Feb. 2014).
Anonymous "Blog della Parafarmacia Farma Drugstore del Dott. Baronzio Attilio" LisoNatural come comprare una Maserati al prezzo della Ferrari . . . XP055103951, farmadrugstore.blogspot.co.uk/2013/11/lisonatural-come-compare-una-maserati.html, four pages (Nov. 2013).
Anonymous "Plants to combat colds and flu" XP055103963, www.livingmedicine.org/projects/pdf/wh_10.pdf, two pages (Nov. 2010).
Kraft "Symptomatische Phytotherapia bei Husten Stellenwert pflanzlicher Antitussiva und Expektorantien" = "Symptomatic phytotherapy in coughs: Importance of plant antitussives and expectorants" *Pharmazie in Unserer Zeit*, vol. 37, No. 6, pp. 478-483 (Nov. 2008).
Menale et al., "Use of medicinal plants in the South-Eastern area of the Partenio Regional Park (Campania, Southern Italy)" *Journal of Ethnopharmacology*, vol. 153, No. 1, pp. 297-307 (Feb. 2014).
International Search Report for PCT/IB/2014/065643, five pages (dated Apr. 2015).
Written Opinion of the ISA for PCT/IB2014/065643, 12 pages (dated Apr. 2015).

\* cited by examiner

*Primary Examiner* — Michael Barker
*Assistant Examiner* — Deborah A Davis
(74) *Attorney, Agent, or Firm* — Sterne, Kessler, Goldstein & Fox P.L.L.C.

(57) ABSTRACT

The present invention relates to a new composition for use in the treatment of cough comprising, as sole active principles, *Plantago lanceolata* extract, honey, cane sugar, *Thymus* sp. extract and optionally *Sambucus nigra* juice.

13 Claims, 2 Drawing Sheets

PLANT-BASED COMPOSITION FOR USE IN THE TREATMENT OF COUGH

This application is the U.S. national phase of International Application No. PCT/IB2014/065643, filed 27 Oct. 2014, which designated the U.S. and claims priority to Italian Application No. RM2013A000592, filed 25 Oct. 2013; the entire contents of each of which are hereby incorporated by reference.

The present invention relates to a new composition for use in the treatment of cough comprising, as sole active principles, *Plantago lanceolata* extract, honey, cane sugar, *Thymus* sp extract, and optionally *Sambucus nigra* juice.

STATE OF THE PRIOR ART

Classic pharmacological therapy is essentially based on cough suppression by chemical and pharmacological mechanisms. On the basis of their mechanism of action, anticough drugs can be classified into 3 categories:

Mucolytics: increase mucus fluidity, with mechanisms of depolymerization of mucoproteic complexes and of nucleic acids.

Expectorants: increase bronchial secretions and indirectly reduce mucus viscosity.

Sedatives: inhibit the cough centre, eliminating the symptom.

The limitations of anticough drugs lie in their specificity of action and in their side effects: mucolytics only act in moist cough; sedatives are indicated in dry cough only, hindering its physiological action; expectorants have a scarcely rational mechanism of action, so much so that in actual fact they are not prescribed.

Moreover, anticough drugs are scarcely adequate in pediatric age: in fact, mucolytics and central sedatives are contraindicated under age 2 years.

Therefore, a treatment of cough by non-irritating compositions, free from drugs such as, e.g., cortisone-based drugs or antibiotics, which can therefore be used without contraindications due to overdosage of such typologies of drugs and therefore also suitable for pediatric use, is of evident interest in the state of the art. Even though some compositions of undoubted effectiveness do exist, comprising honey and other plant active principles, it is of constant interest to develop alternative formulations that may be, e.g., more effective on some types of pathogens rather than on other ones. This enables to provide valid alternatives to effective products, which, though maintaining features common to valid known products, have a spectrum of activity with different effectiveness on different pathogens.

Throat-soothing products are known which comprise various herbal extracts and honey, like e.g., Ricola drops, which contain honey together with a mixture of 13 herbs, Tannenblut drops, indicated for sore throat and to relieve cough, containing plant extracts from conifer sprouts, sage leaves and peppermint leaves, fennel, anise, thyme, *primula* root, Icelandic moss, lime tree flowers and elderberry flowers, plantain, kidney vetch, sucrose, sugar candy, water and honey; cough syrups containing plant extracts from numerous herbs, propolis and honey.

Also officinal plants- and honey-based syrups for the treatment of cough are known in the literature, like e.g. a syrup reported on the www.livingmedicine.org website, comprised of liquorice, *Althaea* (marsh mallow), plantain, thyme, anise, honey, sugar, glycerin and water. All plants present in the syrup are known for properties beneficial to the respiratory system.

Moreover, a vast number of plants useful for the treatment of cough or of its symptoms are known in the literature; a brief example is comprised of:

1. Antitussive and mucolytic plants, comprising, by way of example:

*Althaea officinalis, Cephaelis ipecacuanha, Cetraria islandica, Drosera rotundifolia, Eucalyptus globulus, Glycyrrhiza glabra, Grindelia* species, *Hedera helix, Malva silvestris, Marrubium vulgaris,* Peppermint, *Myroxylon toluiferum, Origanum mayorana, Papaver somniferum, Pinus* species, *Plantago major, Polygala senega, Primula vulgaris, Styrax tonkinensis, Thymus vulgaris, Tilia cordata, Verbascum thapsus* and many others, each one with specific properties, like e.g. antitussive, expectorant, mucolytic properties, etc.;

2. Plants having an anti-asthmatic action, comprising, by way of example:

*Boswellia serrata, Cola acuminata, Drosera rotundifolia, Ephedra sinica, Ginkgo biloba, Ilex paraguaiensis, Thea sinensis* and many others, etc.

Numerous reviews on officinal plants and their properties are published in the literature. As to the cough topic, e.g., the publication by KRAFT K: "Symptomatische Phytotherapie bei Husten Stellenwert pflanzlicher Antitussiva und Expektorantien", PHARMAZIE IN UNSERER ZEIT, VCH VERLAGSGESELLSCHAFT, WEINHEIM, DE, vol. 37, no. 6, 1 Nov. 2008, pages 478-483, is available Due to the presence of numerous officinal plants useful for the treatment of affections of the respiratory system, the development of natural-based formulations for the treatment of disorders of the respiratory system is of constant interest. Particularly, natural substances-based compositions for the treatment of cough that may also be used in pediatric age are of interest.

SUMMARY OF THE INVENTION

Therefore, the present invention relates to a formulation for the treatment of cough whose components are able to interact synergistically so as to intervene locally with mechanical-physical effects on its physiopathogenetic mechanisms.

The formulation of the invention is able to act with a mainly mechanical effect:

I. on inflammation (which is the factor triggering the cough), by an indirect action carried out through the formation of a protective layer which, on the one hand prevents further contact with external irritating agents and preserves mucous membrane hydration, and on the other hand, thanks to the intervention of anti-oxidizing substances, mitigates the noxious effect of the free radicals produced by infections;

II. on mucus, making it more fluid and therefore more easily removable by physiological clearance mechanisms, by hydration thereof due to water-attracting hydrophilic substances.

Thus, the cough symptom can be mitigated without nullifying its physiological role and promoting a restoration of normal conditions of mucus and mucous membrane.

Therefore, the Authors of the present invention have developed a natural substances-based composition particularly effective for the treatment of cough.

Therefore, the present invention relates to a composition for use in the treatment of cough comprising, as sole active principles, *Plantago lanceolata* extract, cane sugar, honey, thyme extract, optionally comprising also *Sambucus nigra* juice.

The present invention also relates to a process for the preparation of said composition wherein *Plantago lanceolata* and thyme extracts are mixed with honey, cane sugar and one or more natural flavourings, preservative agents, aggregating agents and optionally with *Sambucus nigra* juice and/or pharmaceutically acceptable excipients.

Glossary

For the purposes of the present invention, *Thymus* sp. denotes plants belonging to genus *Thymus*, such as, e.g., *Thymus vulgaris, Thymus serpillum, Thymus Citriodorus, Thymus zygis, Thymus herba barona*. In any point of the present invention the term *Thymus* sp. may be replaced by the term *Thymus vulgaris*. By "tops" or "flowering tops" it is meant the term as commonly used in herbal medicine and in botanical treatises, therefore the aerial ends of the plant which contain leaves, stems (meant as branches and not merely as main stalk of the plant) and flowers, or at least one of these components are meant.

DETAILED DESCRIPTION OF THE FIGURES

For this assay, formulations according to Examples 1 and 2 were used.

Panel 2A shows said percentage for a formulation according to the invention with *Sambucus nigra* juice, whereas Panel 2B shows said percentage for a formulation according to the invention without *Sambucus nigra* juice.

For this assay, formulations according to Samples 1 and 2 were used.

DETAILED DESCRIPTION OF THE INVENTION

Cough is a sudden expiratory manoeuvre that can occur as a reflex or as a voluntary action and has the aim of freeing the respiratory tract from any material present (expectoration), thereby performing a role indispensable to the physiological functioning of the respiratory system.

However, this system for defending the respiratory tract becomes a pathological condition when protracting in time, owing to repeated irritative stimuli (infective agents, irritating substances) causing excessive production of secretions and mucus, which accumulate in the respiratory tract and become a concomitant cause of tussive stimulus.

The mucous membrane lining the respiratory tract plays a protective role of functional barrier between the external environment and the tissues:

a) represents a real physical barrier, protecting underlying tissues from contact with the outside;

b) due to the presence of ciliated cells, with synchronized and unidirectional movements pushes mucus-entrapped foreign matter toward the esophagus;

c) produces secretions and mucus;

d) performs immunological functions, and in the presence of a virus enacts a series of effective defense mechanisms crucial in the antiviral response.

Part of its protective function is performed by the mucus covering it, which is an adhesive, viscoelastic gel produced by goblet cells and whose main macromolecules are glycoproteins.

It should be taken into account that the mucus, which under normal conditions has a protective role, in case of infection or other type of irritation becomes itself cause of cough: in fact, an overproduction and a higher viscosity thereof are witnessed.

The main mechanisms which onset from an infective and/or irritative event causing phlogosis of ear and throat can be described as follows:

1. direct involvement of larynx and trachea, due to their nearness and to the close communication relationships with mouth, pharynx and nose;

2. transport of inflammation mediators produced in the infection site, through the bloodstream, to the lower respiratory tract, where they initiate an inflammatory response; studies on guinea pigs and humans demonstrated that chemical-type sensory stimuli afferent from nose or esophagus can increase sensitivity to cough of the central nerve pathways, contributing to the "hypertussive" state accompanying inflammatory diseases of the respiratory tract, nose and esophagus.

3. in the post-nasal drip a continuous presence of mucus occurs, often in the form of viscous filaments difficult to expel from the nasopharynx, which by descending along the pharynx irritates it. This irritation causes a loss of coordination between nerves and muscles of trachea and esophagus, so that part of excess secretions pour into the larynx, causing a mechanical stimulation thereof which translates into a persistent, continuous and irritating cough, very frequent in children.

An important role in cough mechanisms is performed by the different types of receptors localized at the esophagus level, whose stimulation can trigger cough by various mechanisms:

stimulation of tension mechanosensors by means of the repeated attempts at deglutition of the copious and viscous mucus in case of infective events;

stimulation of mucosal receptors sensitive to light pressure stimuli exerted by mucous filaments stagnating between hypopharynx and esophagus stimulation of nociceptors by inflammation mediators produced locally and carried by mucus to other sites (alike stimulation mechanisms have been demonstrated in guinea pig, even with acidic chemical stimuli).

On the basis of the fact that both the physiological mechanisms for protection of respiratory tract mucous membranes and the pathogenetic processes of cough are actually based on mechanical-type mechanisms (mucus and intact mucosa on the one hand, mucus overproduction and mechanical stimulation on the other hand) the Inventors deemed that intervening with an action of mucous membrane protection could be the only approach really effective.

Therefore, the therapeutic approach to cough as described above required the development of a formulation that be active in its complexity, i.e. that its components be able to interact synergistically so as to intervene locally with mechanico-physical effects on its physio-pathogenetic mechanisms.

Bearing in mind such aim, a composition was made for use in the treatment of cough, comprising *Plantago lanceolata*, a.k.a. "plantain", extract, cane sugar, honey, *Thymus* sp. extract, a.k.a. "thyme"), optionally comprising also *Sambucus nigra*, a.k.a. "elderberry", juice.

Of *Plantago lanceolata*, leaves could be used; as to *Thymus* sp., tops as defined above, and/or leaves of plants selected from *Thymus vulgaris, Thymus serpillum, Thymus Citriodorus, Thymus zygis, Thymus herba barona*, or mixtures thereof could be used. In a preferred embodiment, *Thymus vulgaris* extract will be used.

*Sambucus nigra* juice could be juice obtained from frozen and/or fresh *Sambucus nigra* berries, and could be used as such, diluted, concentrated (e.g., 50, 55, 60, 65 Brix).

The juice could be prepared according to standard techniques known to a person skilled in the art.

According to the present invention the extracts could be hydroalcoholic extracts, lyophilised extracts, dry extracts, extracts dried by spray-drying technique (different from lyophilisation), soft extracts or mixtures thereof.

The preparation of such types of extracts can be carried out with well-known technologies, therefore no further indication is necessary for a technician in the field to carry out the present invention.

The composition according to the invention is suitable for use on adult, geriatric-age, gestating, pediatric-age patients. The embodiment comprising also *Sambucus nigra* juice is preferred for pediatric use.

In order to verify the effectiveness of the composition of the invention, comparative assays were carried out between the composition of the invention and plant-based antitussive syrups described in the literature, in which there were compared the mucoadhesive abilities, and therefore the abilities of respiratory tract mucous membranes protection, which are fundamental for the effectiveness of the composition as explained above. The syrups as described in Tables 2 and 3 below were compared with the syrup reported in the state of the art above, comprised of liquorice, *Althaea*, plantain, thyme, anise, honey, sugar, glycerin and water, and the assays carried out demonstrated that the mucoadhesive properties of the compositions of the invention, in form of syrup, are about twice those of the syrup described in the state of the art.

Since the syrup described in the state of the prior art comprises some of the active principles present in the composition of the invention together with others, the comparison carried out demonstrated that the selection of only some active principles and their coformulation is more effective than a mixture comprising also such active principles together with others known in the literature as antitussives.

The fact that the effectiveness of different mixtures of officinal plants is strictly dependent on the selected plants is anyhow known to the technician in the field, therefore it is not obvious to single out, among the numerous officinal plants known in the literature, which mixtures be more effective than others.

The preparation of the extracts, as already mentioned, could be carried out according to any technique known to a person skilled in the art, in one specific embodiment said extracts could be lyophilised extracts.

The honey could be bee honey, honeydew honey or a mixture thereof, and could be used it also in a lyophilised form or in any form.

The formulation could then comprise thickening agents, flavourings, and preservative agents of natural or synthetic origin or other technological adjuvants that the technician skilled in the field could select according to the state of the art. By mere way of example, juices (such as lemon juice, i.e. *Citrus limon*), flavours (e.g., natural orange flavour (*Citrus aurantium*), natural lemon flavour (*Citrus limon*), natural peach flavour (*Prunus persica*), natural strawberry flavour (*Fragaria* sp.), natural blackberry flavour (*Rubus ulmifolius*)), thickening agents (such as xanthan gum, gum arabic) could be selected.

Therefore, the above-described composition could consist in *Plantago lanceolata* extract, cane sugar, honey, *Thymus* sp. extract and suitable excipients, flavours, preservative agents, thickening agents, or could alternatively consist in *Plantago lanceolata* leaf extract, cane sugar, honey, *Thymus* sp. extract, *Sambucus nigra* juice and suitable excipients, flavours, preservative agents, thickening agents.

Table 1 below synthetically reports for the different functional components (active principles) listed above, the physico-mechanical effect carried out and the plant or natural substance from which it derives.

| Functional components | Mechanical-physical effect carried out | Natural source |
| --- | --- | --- |
| Polysaccharides | Protective film against irritating agents, hydration contribution to secretions | *Plantago lanceolata* extract |
| Sugary substances | adhesivity (viscosity-consistence), increase of salivation and of the water part of mucous membrane secretions | Honey, Cane sugar |
| Antioxidizing substances | Protection from damage due to free radicals | *Thymus* sp. extract, *Sambucus nigra* juice, Honey |

The compositions of the invention are therefore comprised of a set of functional substances having chemico-physical properties such as to perform overall a mucus-fluidifying effect and an effect of protecting the mucous membrane at the level of the application site represented by the upper respiratory tract.

These effects are obtained thanks to the synergy that develops among the different components:

I. the mucoadhesive property characteristic of *Plantago lanceolata* polysaccharides, together with the viscosity of the entire formulation, enable an uniform distribution of the product and the formation of a protective film with barrier effect;

II. the high sugar concentration given by honey and sugar increases the water content of mucus, which becomes more fluid (indirect fluidifying action) and therefore more easily removable by ciliary movements; also the higher hydration of the same mucous membrane mitigates the irritation thereof;

III. the marked anti-oxidizing properties of honey, *Thymus* sp. and *Sambucus nigra* juice indirectly intervene in the local inflammatory processes: by radical scavenging mechanisms, they reduce the concentration of free radicals which form at the level of the irritated mucous membrane.

By the above-described mechanisms, the formulations mitigate the susceptibility of the mucous membrane, reducing the tussive attacks and promoting restoration of the physiological state of mucus and mucous membrane.

For these reasons, they can be useful in the treatment of dry cough, productive cough, URTI (upper respiratory tract infections)-associated cough, or even post nasal drip cough.

Moreover, the selection of the components of the above-described composition proved particularly active against some specific pathogens (data not shown).

According to the present invention, the composition will be made for oral administration and could be made in the form of capsule, tablet, pill, granules, powder, syrup, fluid, elixir, hard gelatine, soft gelatine, suspension, emulsion, solution.

For oral administration the composition could be made in the form of daily unit dosages or of fractions of daily unit dosages (e.g., 2, 3, 4, 5, 6, or more capsules, tablets, lozenges, granule or powder single-doses, syrup or fluid, or gelatines could be taken over the day, in accordance with the judgment of the treating doctor), and may contain conventional excipients including, e.g., binding agents, like gum (gum tragacanth, gum arabic), animal gelatine and polyvinylpyrrolidone; diluents, such as sugar, polyalcohols (sorbitol, mannitol, xylitol), maltodextrins, inorganic salts (bibasic calcium phosphate, calcium carbonate); disintegrants, like rice starch, corn starch and potato starch; lubricants, like magnesium stearate, polyethylene glycols with different molecular weights; glidants, like colloidal silica; antiadhering agents, such as, e.g., talc; wetting agents like sodium laurylsulphate.

The composition could also be made in a liquid or semi-liquid form, as a suspension, emulsion, solution for oral administration, and could optionally contain natural flavourings giving a palatable taste thereto.

The composition in the form of powder or granule could be pre-metered in suitable containers and ready for use, either by ingestion as such or to be resuspended in an appropriate liquid such as water, tea, etc. In this case as well, the composition could contain natural flavourings giving a palatable taste thereto.

Evidently, all of the above-indicated excipients could be used in a pharmaceutically acceptable grade.

In one embodiment, the composition as described herein, in any one of the above-indicated embodiments, could be in the form of pharmaceutical composition, i.e. comprise pharmaceutical-grade ingredients or it could be or be introduced into a medical food or into a medical device.

The composition according to the present description could be made in the form of pharmaceutical composition or of medical device according to any one of the classes described in Directive 93/42/EEC on medical devices (comprising also substances and not only "devices" in the sense of objects).

In case of a syrup there could be used, besides the above-described components and one or more of the agents previously described (preservative agents, aggregating agents (aggregants), excipients, flavouring, etc.).

Therefore, in a specific embodiment of the present invention the composition could be consisting of or comprise the following components:

TABLE 2

Adults

CANE SUGAR
HONEY
EXCIPIENTS AND/OR CARRIERS
LEMON JUICE
LYOPHILISED

TABLE 2-continued

Adults

PLANTAGO LANCEOLATA EXTRACT
NATURAL FLAVOURINGS, POWDER
LYOPHILISED THYMUS SP. EXTRACT
AGGREGANT, POWDER

TABLE 3

Adults and/or children

CANE SUGAR
HONEY
EXCIPIENTS AND/OR CARRIERS
SAMBUCUS NIGRA JUICE
LEMON JUICE
LYOPHILISED PLANTAGO LANCEOLATA EXTRACT
NATURAL FLAVOURINGS, POWDER
LYOPHILISED THYMUS SP. EXTRACT
AGGREGANT, POWDER

TABLE 4

| General composition | % w/w |
|---|---|
| CANE SUGAR | 20-60 |
| HONEY | 10-80 |
| EXCIPIENTS AND/OR CARRIERS | 10-80 |
| LEMON JUICE | 0.5-3 |
| LYOPHILISED PLANTAGO LANCEOLATA LEAVES EXTRACT | 0.1-1 |
| SAMBUCUS NIGRA JUICE | 0-3 |
| NATURAL FLAVOURINGS, POWDER | 0.1-2.7 |
| LYOPHILISED THYMUS VULGARIS EXTRACT | 0.01-0.5 |
| XANTHAN GUM, POWDER | 0.01-1 |

TABLE 5

| Composition without Sambucus nigra juice | % w/w |
|---|---|
| CANE SUGAR | 20-60 |
| HONEY | 10-80 |
| EXCIPIENTS AND/OR CARRIERS | 10-80 |
| LEMON JUICE | 0.5-3 |
| LYOPHILISED PLANTAGO LANCEOLATA LEAVES EXTRACT | 0.1-1 |
| NATURAL ORANGE FLAVOUR, POWDER | 0.1-1.5 |
| LYOPHILISED THYMUS VULGARIS EXTRACT | 0.01-0.5 |
| NATURAL LEMON FLAVOUR, POWDER | 0.05-0.5 |
| NATURAL PEACH FLAVOUR, POWDER | 0.01-0.7 |
| XANTHAM GUM, POWDER | 0.01-1 |

TABLE 6

| Composition with Sambucus nigra juice | % w/w |
|---|---|
| CANE SUGAR | 20-60 |
| HONEY | 10-80 |
| EXCIPIENTS AND/OR CARRIERS | 10-80 |
| LEMON JUICE | 0.5-3 |
| LYOPHILISED PLANTAGO LANCEOLATA LEAVES EXTRACT | 0.1-1 |
| SAMBUCUS NIGRA JUICE | 0-3 |

TABLE 6-continued

| Composition with *Sambucus nigra* juice | % w/w |
|---|---|
| LYOPHILISED *THYMUS VULGARIS* EXTRACT | 0.01-0.5 |
| NATURAL STRAWBERRY FLAVOUR, POWDER | 0.05-1 |
| NATURAL BLACKBERRY FLAVOUR, POWDER | 0.05-1 |
| XANTHAM GUM, POWDER | 0.01-1 |

In case the formulation be liquid, for instance a syrup, the composition could consist in the following components

TABLE 7

| Syrup | % w/w |
|---|---|
| CANE SUGAR | 20-60 |
| HONEY | 10-80 |
| DEIONIZED WATER and/or other suitable carrier or excipient | 10-80 |
| LEMON JUICE | 0.5-3 |
| LYOPHILISED *PLANTAGO LANCEOLATA* LEAVES EXTRACT | 0.1-1 |
| *SAMBUCUS NIGRA* JUICE | 0-3 |
| NATURAL FLAVOURINGS, POWDER | 0.16-2.7 |
| LYOPHILISED *THYMUS VULGARIS* EXTRACT | 0.01-0.5 |
| XANTHAM GUM, POWDER | 0.01-1 |

TABLE 8

| Syrup without *Sambucus nigra* juice | % w/w |
|---|---|
| CANE SUGAR | 20-60 |
| HONEY | 10-80 |
| DEIONIZED WATER and/or other suitable carrier or excipient | 10-80 |
| LEMON JUICE | 0.5-3 |
| LYOPHILISED *PLANTAGO LANCEOLATA* LEAVES EXTRACT | 0.1-1 |
| NATURAL ORANGE FLAVOUR, POWDER | 0.1-1.5 |
| LYOPHILISED *THYMUS VULGARIS* EXTRACT | 0.01-0.5 |
| NATURAL LEMON FLAVOUR, POWDER | 0.05-0.5 |
| NATURAL PEACH FLAVOUR, POWDER | 0.01-0.7 |
| XANTHAM GUM, POWDER | 0.01-1 |

TABLE 9

| Syrup with *Sambucus nigra* juice | % w/w |
|---|---|
| CANE SUGAR | 20-60 |
| HONEY | 10-80 |
| DEIONIZED WATER and/or other suitable carrier or excipient | 10-80 |
| LEMON JUICE | 0.5-3 |
| LYOPHILISED *PLANTAGO LANCEOLATA* LEAVES EXTRACT | 0.1-1 |
| *SAMBUCUS NIGRA* JUICE | 0-3 |
| LYOPHILISED *THYMUS VULGARIS* EXTRACT | 0.01-0.5 |
| STRAWBERRY NATURAL FLAVOUR, POWDER | 0.05-1 |
| NATURAL BLACKBERRY FLAVOUR, POWDER | 0.05-1 |
| XANTHAM GUM, POWDER | 0.01-1 |

The present invention also relates to a process for the preparation of said composition, in which the sole active principles are: *Plantago lanceolata* and *Thymus* sp extracts, and optionally *Sambucus nigra* juice as described above, mixed with honey and cane sugar, and such active principles are then mixed with one or more natural flavourings, preservative agents, thickening agents and/or pharmaceutically acceptable excipients.

Lastly, the present invention also relates to a method for the treatment of dry cough, productive cough, URTI (upper respiratory tract infections)—associated cough, post nasal drip comprising the administration of a therapeutically active dosage of the composition of the invention to a patient in need thereof, wherein said patient can also be in pediatric age, geriatric age, gestating.

Formulation Examples

Hereinafter, some specific examples of liquid formulation are provided which are not to be understood as a limitation of the application.

TABLE 10

| COMPOSITION EXAMPLE 1 | % w/w |
|---|---|
| CANE SUGAR | 45 |
| HONEY | 33 |
| DEIONIZED WATER and/or other suitable carrier or excipient | 20 |
| LEMON JUICE | 0.6 |
| LYOPHILISED *PLANTAGO LANCEOLATA* LEAVES EXTRACT | 0.58 |
| NATURAL ORANGE FLAVOUR, POWDER | 0.2 |
| LYOPHILISED *THYMUS VULGARIS* EXTRACT | 0.3 |
| NATURAL LEMON FLAVOUR, POWDER | 0.1 |
| NATURAL PEACH FLAVOUR, POWDER | 0.15 |
| XANTHAM GUM, POWDER | 0.07 |

TABLE 11

| COMPOSITION EXAMPLE 2 | % w/w |
|---|---|
| CANE SUGAR | 30 |
| HONEY | 35 |
| DEIONIZED WATER and/or other suitable carrier or excipient | 30 |
| *SAMBUCUS NIGRA* JUICE | 2 |
| LEMON JUICE | 0.7 |
| LYOPHILISED *PLANTAGO LANCEOLATA* LEAVES EXTRACT | 0.8 |
| NATURAL STRAWBERRY FLAVOUR, POWDER | 0.55 |
| NATURAL BLACKBERRY FLAVOUR, POWDER | 0.5 |
| LYOPHILISED *THYMUS VULGARIS* EXTRACT | 0.25 |
| XANTHAM GUM, POWDER | 0.2 |

TABLE 12

| COMPOSITION EXAMPLE 3 | % w/w |
|---|---|
| CANE SUGAR | 49 |
| HONEY | 29 |
| DEIONIZED WATER and/or other suitable carrier or excipient | 20 |
| LEMON JUICE | 0.56 |
| LYOPHILISED PLANTAGO LANCEOLATA LEAVES EXTRACT | 0.76 |
| NATURAL ORANGE FLAVOUR, POWDER | 0.2 |
| LYOPHILISED *THYMUS VULGARIS* EXTRACT | 0.52 |
| NATURAL LEMON FLAVOUR, POWDER | 0.1 |
| NATURAL PEACH FLAVOUR, POWDER | 0.15 |
| XANTHAM GUM, POWDER | 0.07 |

TABLE 13

| COMPOSITION EXAMPLE 4 | % w/w |
|---|---|
| CANE SUGAR | 34 |
| HONEY | 31 |
| DEIONIZED WATER and/or other suitable carrier or excipient | 29 |
| *SAMBUCUS NIGRA* JUICE | 2.6 |
| LEMON JUICE | 0.7 |
| LYOPHILISED *PLANTAGO LANCEOLATA* LEAVES EXTRACT | 0.9 |
| NATURAL STRAWBERRY FLAVOUR, POWDER | 0.65 |
| NATURAL BLACKBERRY FLAVOUR, POWDER | 0.5 |
| LYOPHILISED *THYMUS VULGARIS* EXTRACT | 0.45 |
| XANTHAM GUM, POWDER | 0.2 |

TABLE 14

| COMPOSITION EXAMPLE 5 | % w/w |
|---|---|
| CANE SUGAR | 40 |
| HONEY | 38 |
| DEIONIZED WATER and/or other suitable carrier or excipient | 20 |
| LEMON JUICE | 0.6 |
| LYOPHILISED *PLANTAGO LANCEOLATA* LEAVES EXTRACT | 0.58 |
| NATURAL ORANGE FLAVOUR, POWDER | 0.2 |
| LYOPHILISED *THYMUS VULGARIS* EXTRACT | 0.3 |
| NATURAL LEMON FLAVOUR, POWDER | 0.1 |
| NATURAL BLACKBERRY FLAVOUR, POWDER | 0.15 |
| XANTHAM GUM, POWDER | 0.07 |

TABLE 15

| COMPOSITION EXAMPLE 6 | % w/w |
|---|---|
| CANE SUGAR | 48 |
| HONEY | 30 |
| DEIONIZED WATER and/or other suitable carrier or excipient | 20 |
| LEMON JUICE | 0.6 |
| LYOPHILISED *PLANTAGO LANCEOLATA* LEAVES EXTRACT | 0.58 |
| NATURAL ORANGE FLAVOUR, POWDER | 0.2 |
| LYOPHILISED *THYMUS VULGARIS*, EXTRACT | 0.3 |
| NATURAL STRAWBERRY FLAVOUR, POWDER | 0.15 |
| NATURAL PEACH FLAVOUR, POWDER | 0.10 |
| XANTHAM GUM, POWDER | 0.07 |

Experimental Examples

The following experimental examples have the purpose of illustrating some of the assays performed on the composition of the present invention.

1. Mucoadhesion Assay

The mucoadhesive effect of a product, contributing to the formation of the protective film on the mucous membranes, can be assessed by suitable in vitro models.

The model used demonstrates that the mucoadhesivity of products intended for treatment of the mucous membranes can be determined by assessment of the percentage of lectin-glycoprotein bonding inhibition. Mucosal buccal cells are initially treated with biotinylated lectin (Con-A), a protein contained in some leguminosae (*Canavalia ensiformis*) having a high affinity for the glucoside and mannoside residues present in the glycoproteins of the membrane. The sites of the glycoproteins of the mucous membranes will thus be all engaged with the biotinylated lectin (treated with biotin, i.e. vitamin H). The cells, treated with biotinylated lectin, are charged with streptavidin peroxidase, making it possible to form the protein/glucose/lectin/biotin/streptavidin peroxidase complex thanks to the high affinity between biotin and streptavidin.

At this point, the cells are washed and the protein/glucose/lectin/biotin/streptavidin peroxidase complex is quantified, assessing peroxidase activity, by means of a reaction of oxidation of the ortho-phenylenediamine (colorimetric assessment).

In fact, the protein/glucose/lectin/biotin/streptavidin peroxidase complex will catalyse the oxidation reaction:

O-phenylenediamine $\xrightarrow[\text{Strep. perox.}]{\text{H}_2\text{O}_2}$ 2,3-diaminophenazine (yellow)

The intensity of the yellow/orange colouration of the solution (measured using a spectrophotometer with $\lambda=450$ nm) is proportional to the quantity of glycoprotein/lectin bonds and therefore to the quantity of available sites (glycoproteins) for mucoadhesion.

The absorbency value thus determined constitutes the "control".

When determining the mucoadhesivity of a product, the cells are treated preliminarily with this product (incubation at 30° C. for 15 minutes before the treatment with lectin).

If the product under examination contains mucoadhesive substances, these will bind to the glucoside and mannoside sites present in the glycoproteins of the membrane.

In the next phase, adding the sequence of biotinylated lectin, streptavidin peroxidase and ortho-phenylenediamine there will be obtained a less intense colouration, compared to the control, and this since part of the glucoside sites available for bonding with the Con-A were already occupied by the mucoadhesive substances present in the product to be assayed. In fact, the initial bonding between the mucoadhesive substances contained in the product to be assayed and the glucoside sites partly compromises the subsequent conjugation of the Con-A with the streptavidin peroxidase complex and the subsequent development of colour after addition of oxygenated water.

The decrease in the absorbency value is proportional to the ability of the substances under examination to "mucoadhere" to mucosal cells.

The mucoadhesive ability is expressed as a percentage of inhibition of glycoprotein/lectin bonding, and represents the percentage of mucosal sites occupied by the product according to the expression:

Percentage of mucoadhesion of the product=(1−abs sample/abs control)×100

Furthermore, in addition to the mucoadhesive ability, it is also assessed the resistance of the mucoadhesive layer to the action of the salivary solution with which it comes to contact.

To this end, in a second phase of the experiment, the resistance over time (0.5-2 h) of the mucoadhesivity of the product after exposure to a continuous flow of artificial salivary solution.

To perform this assay, a system of Franz cells was employed, these cells generally being used in the assessment of percutaneous absorption of a substance or for the study of other processes of permeation through natural or artificial membranes.

In the experiment, the buccal cellular cultures were deposed in the donor and were treated with the product diluted 1:2 (a dilution in all likelihood nearer to the real conditions that might occur in vivo). The donor was then fed with a continuous flow (2 ml/min.) of artificial salivary solution, by a peristaltic pump.

At the base of the donor, in the zone of separation with the receptor, a cellulose acetate membrane was placed, capable of allowing outflow of the salivary solution from the donor to the receptor, retaining the mucosal cells in the donor. The salivary flow through the mucosal cells treated with the product under examination was regularly discontinued after 0.5, 1, 2 hours and the cells of the donor transferred into a suitable test tube for mucoadhesivity assessment.

In light of the results obtained, it is possible to state that the product, demonstrating to possess good, resistant mucoadhesivity, can play an interesting protective role on mucosal cells of the oral tract.

In order to mime the natural dilution of a syrup in the oral cavity, the mucoadhesivity assays were carried out on a product diluted 1:2; for greater completeness, also the mucoadhesivity of the product diluted 1:5 was assayed.

Figure 1:
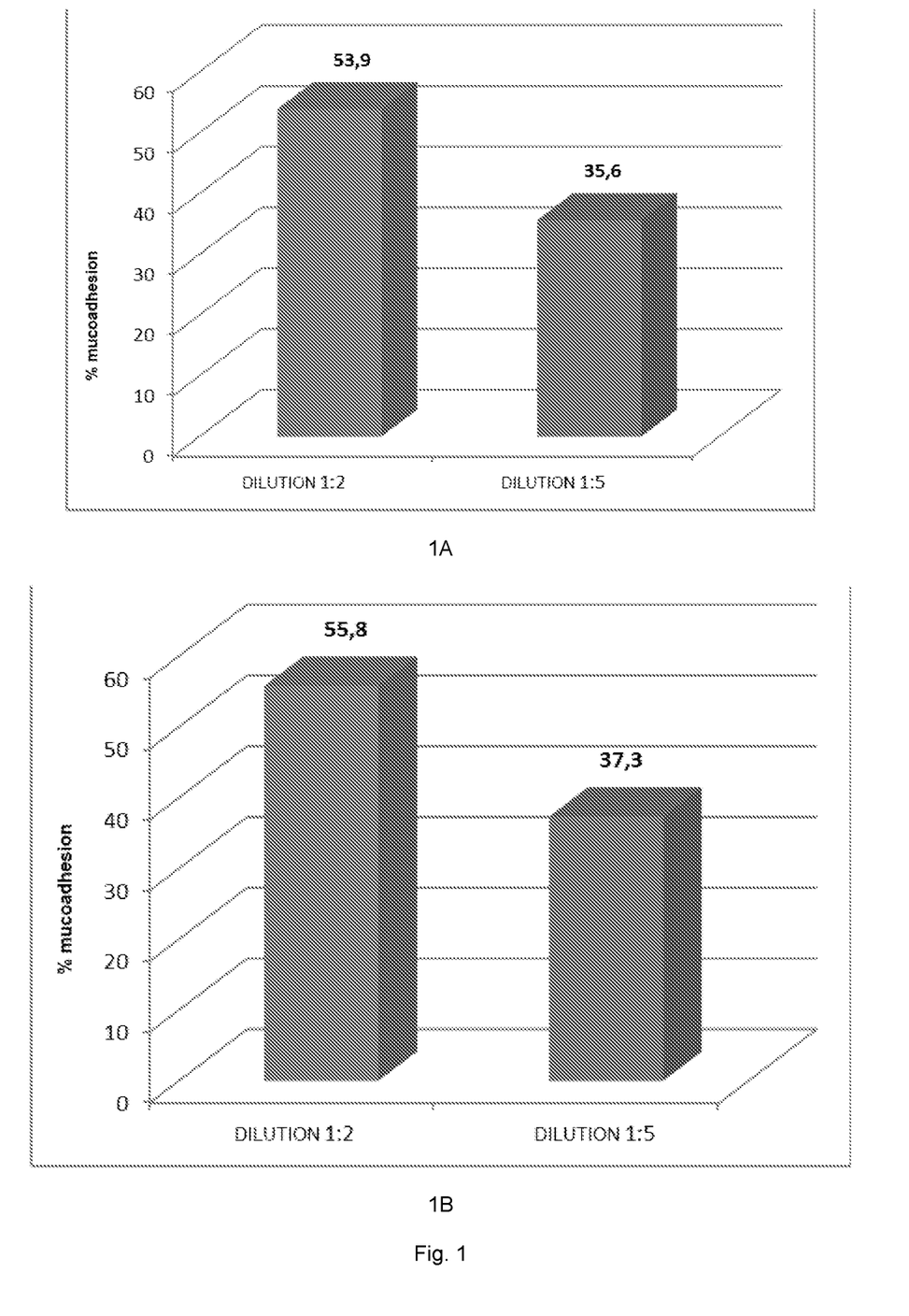
In FIG. 1, the mucoadhesivity percentage of the diluted (1:2 and 1:5) product towards human buccal cells is reported. Panel 1A shows said percentage for a formulation according to the invention with *Sambucus nigra* juice, whereas Panel 1B shows said percentage for a formulation according to the invention without *Sambucus nigra* juice.
Figure 2:
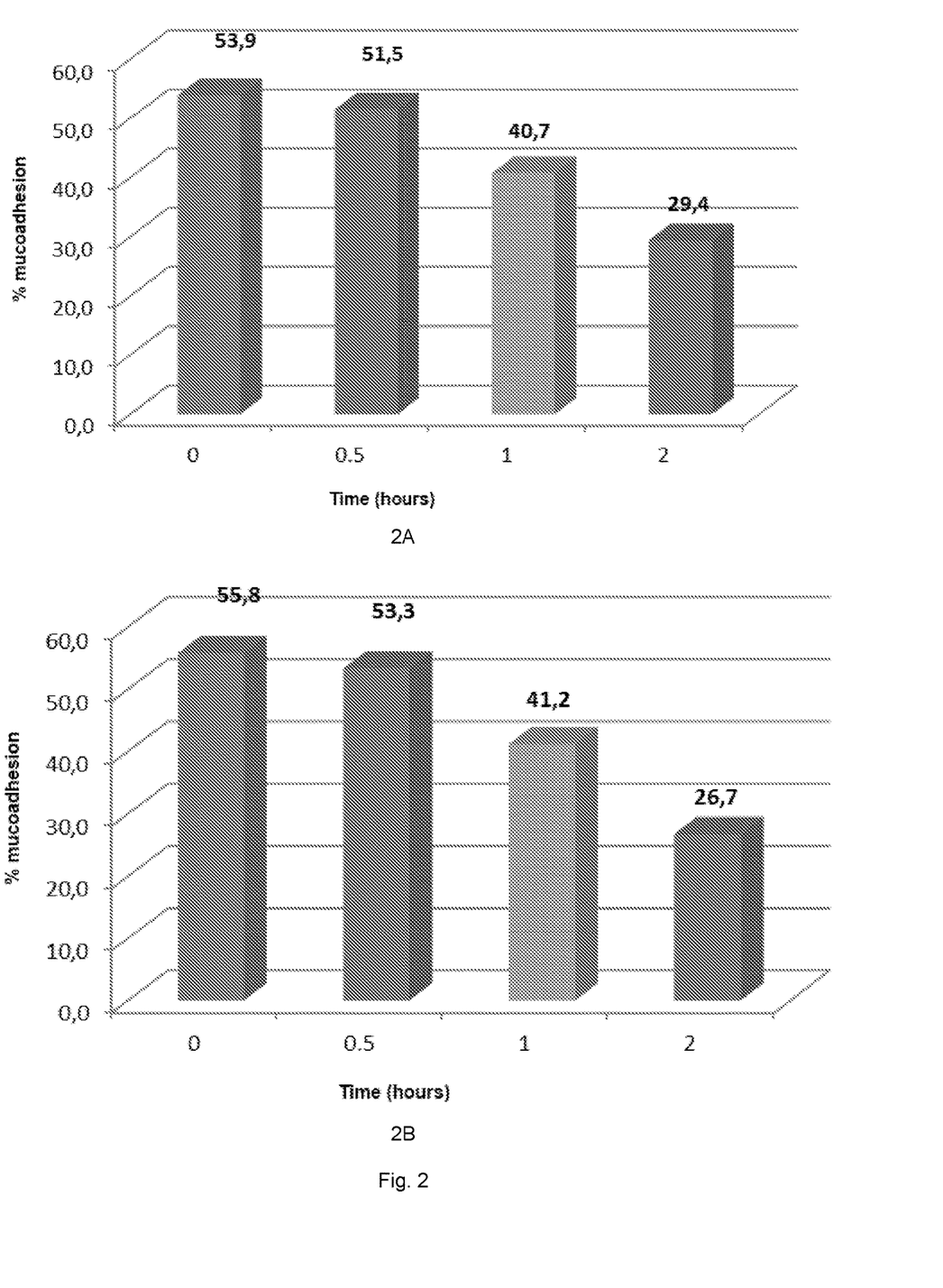
In FIG. 2, it is reported the resistance of the mucoadhesive layer obtained with the product diluted 1:2 at different times, 0.5 h, 1 h, and 2 h, to a simulated salivary solution (0.9% NaCl physiological solution).

The mucoadhesivity percentage of the diluted (1:2 and 1:5) product towards human buccal cells is reported in FIG. 1.

the resistance of the mucoadhesive layer obtained with the product diluted 1:2 at different times, 0.5 h, 1 h and 2 h, towards a simulated salivary solution (0.9% NaCl physiological solution) is shown in FIG. 2.

2. Assessment of the Antibacterial Effect of the Composition According to the Invention Preliminary data on assays performed as follows show specific antibacterial abilities of the composition of the invention.

Pharyngeal tampons were collected from consenting patients and stored in refrigerator at 4° C. until treatment.

a. The tampons are dissolved in about 2 ml of sterile physiological solution at 35° C. The microbial suspensions are agitated with a vortex for 2 minutes, centrifuged to eliminate exfoliated cells, after spectrophotometric reading at 600 nm brought to the same concentration with physiological solution ($10^8$ cells/ml). The microbial suspension in physiological solution are subdivided into various aliquots that are then stored at −80° C. in the presence of 20% glycerol.

b. Aliquots of the same sample are seeded in broth in the presence or in the absence of the composition of the invention. At set times (4-24 h) one aliquot of each experimental sample is seeded on solid media to determine the total microbial count, and on differential media to determine the genus of the microorganisms present.

c. A further aliquot is grown in 96-well plates to determine the ability to form biofilm in the presence and in the absence of the composition according to the invention.

d. Lastly, another aliquot is added to cell monolayers (BEAS-2B ATCC® CRL-9609) pretreated with the composition of the invention, and after 1-2 h of incubation the number and the genus of the bacteria that have adhered to epithelial monolayers by seeding on selective media are assessed.

The preliminary data obtained show a specific antibacterial activity of the composition according to the invention, with respect to other compositions used as comparative assays.

The invention claimed is:

1. A method of treating a cough in a subject in need thereof, comprising: administering a therapeutically-effective composition consisting of: cane sugar, honey, deionized water, lemon juice, lyophilized *Plantago lanceolata* extract, lyophilized *Thymus* sp. extract, natural orange flavor, natural lemon flavor, natural peach flavor, and xanthan gum;
wherein said composition is in the form of a syrup, and wherein said cough is a dry cough, productive cough, upper respiratory tract infection (URTI)-associated cough, and/or post-nasal drip cough.

2. A method of treating a cough in a subject in need thereof, comprising: administering a therapeutically-effective composition consisting of: cane sugar, honey, deionized water, lemon juice, lyophilized *Plantago lanceolata* extract, lyophilized *Thymus* sp. extract, *Sambucus nigra* juice, natural strawberry flavor, natural blackberry flavor, and xanthan gum;
wherein said composition is in the form of a syrup, and wherein said cough is a dry cough, productive cough, upper respiratory tract infection (URTI)-associated cough, and/or post-nasal drip cough.

3. A method of treating a cough in a subject in need thereof, comprising:
administering a therapeutically-effective composition consisting of: cane sugar, honey, deionized water, lemon juice, lyophilized *Plantago lanceolata* extract, lyophilized *Thymus* sp. extract, natural orange flavor, natural lemon flavor, natural blackberry flavor, and xanthan gum;

wherein said composition is in the form of a syrup, and wherein said cough is a dry cough, productive cough, upper respiratory tract infection (URTI)-associated cough, and/or post-nasal drip cough.

4. A method of treating a cough in a subject in need thereof, comprising:

administering a therapeutically-effective composition consisting of: cane sugar, honey, deionized water, lemon juice, lyophilized *Plantago lanceolata* extract, lyophilized *Thymus* sp. extract, natural orange flavor, natural strawberry flavor, natural peach flavor, and xanthan gum;

wherein said composition is in the form of a syrup, and wherein said cough is a dry cough, productive cough, upper respiratory tract infection (URTI)-associated cough, and/or post-nasal drip cough.

5. The method of claim 1, wherein said composition consists of:

|  | % w/w |
|---|---|
| CANE SUGAR | 20-60 |
| HONEY | 10-80 |
| DEIONIZED WATER | 10-80 |
| LEMON JUICE | 0.5-3 |
| LYOPHILIZED *PLANTAGO LANCEOLATA* LEAVES EXTRACT | 0.1-1 |
| NATURAL ORANGE FLAVOR, POWDER | 0.1-1.5 |
| LYOPHILIZED *THYMUS VULGARIS* EXTRACT | 0.01-0.5 |
| NATURAL LEMON FLAVOR, POWDER | 0.05-0.5 |
| NATURAL PEACH FLAVOR, POWDER | 0.01-0.7 |
| XANTHAM GUM, POWDER | 0.01-1. |

6. The method of claim 2, wherein the composition consists of:

|  | % w/w |
|---|---|
| CANE SUGAR | 20-60 |
| HONEY | 10-80 |
| DEIONIZED WATER | 10-80 |
| LEMON JUICE | 0.5-3 |
| LYOPHILIZED *PLANTAGO LANCEOLATA* LEAVES EXTRACT | 0.1-1 |
| *SAMBUCUS NIGRA* JUICE | 0-3 |
| LYOPHILIZED *THYMUS VULGARIS* EXTRACT | 0.01-0.5 |
| NATURAL STRAWBERRY FLAVOR, POWDER | 0.05-1 |
| NATURAL BLACKBERRY FLAVOR, POWDER | 0.05-1 |
| XANTHAM GUM, POWDER | 0.01-1. |

7. The method of claim 3, wherein said composition consists of:

|  | % w/w |
|---|---|
| CANE SUGAR | 20-60 |
| HONEY | 10-80 |
| DEIONIZED WATER | 10-80 |
| LEMON JUICE | 0.5-3 |
| LYOPHILIZED *PLANTAGO LANCEOLATA* LEAVES EXTRACT | 0.1-1 |
| NATURAL ORANGE FLAVOR, POWDER | 0.1-1.5 |
| LYOPHILIZED *THYMUS VULGARIS* EXTRACT | 0.01-0.5 |
| NATURAL LEMON FLAVOR, POWDER | 0.05-0.5 |
| NATURAL BLACKBERRY FLAVOR, POWDER | 0.01-0.7 |
| XANTHAM GUM, POWDER | 0.01-1. |

8. The method of claim 4, wherein said composition consists of:

|  | % w/w |
|---|---|
| CANE SUGAR | 20-60 |
| HONEY | 10-80 |
| DEIONIZED WATER | 10-80 |
| LEMON JUICE | 0.5-3 |
| LYOPHILIZED *PLANTAGO LANCEOLATA* LEAVES EXTRACT | 0.1-1 |
| NATURAL ORANGE FLAVOR, POWDER | 0.1-1.5 |
| LYOPHILIZED *THYMUS VULGARIS* EXTRACT | 0.01-0.5 |
| NATURAL STRAWBERRY FLAVOR, POWDER | 0.05-1 |
| NATURAL PEACH FLAVOR, POWDER | 0.01-0.7 |
| XANTHAM GUM, POWDER | 0.01-1. |

9. The method of claim 5, wherein said composition consists of:

|  | % w/w |
|---|---|
| CANE SUGAR | 45 |
| HONEY | 33 |
| DEIONIZED WATER and/or other suitable carrier or excipient | 20 |
| LEMON JUICE | 0.6 |
| LYOPHILIZED *PLANTAGO LANCEOLATA* LEAVES EXTRACT | 0.58 |
| NATURAL ORANGE FLAVOR, POWDER | 0.2 |
| LYOPHILIZED *THYMUS VULGARIS* EXTRACT | 0.3 |
| NATURAL LEMON FLAVOR, POWDER | 0.1 |
| NATURAL PEACH FLAVOR, POWDER | 0.15 |
| XANTHAM GUM, POWDER | 0.07. |

10. The method of claim 7, wherein said composition consists of:

|  | % w/w |
|---|---|
| CANE SUGAR | 40 |
| HONEY | 38 |
| DEIONIZED WATER | 20 |
| LEMON JUICE | 0.6 |
| LYOPHILIZED *PLANTAGO LANCEOLATA* LEAVES EXTRACT | 0.58 |
| NATURAL ORANGE FLAVOR, POWDER | 0.2 |
| LYOPHILIZED *THYMUS VULGARIS* EXTRACT | 0.3 |
| NATURAL LEMON FLAVOR, POWDER | 0.1 |
| NATURAL BLACKBERRY FLAVOR, POWDER | 0.15 |
| XANTHAM GUM, POWDER | 0.07. |

11. The method of claim 6, wherein said composition consists of:

|  | % w/w |
|---|---|
| CANE SUGAR | 30 |
| HONEY | 35 |
| DEIONIZED WATER | 30 |
| *SAMBUCUS NIGRA* JUICE | 2 |
| LEMON JUICE | 0.7 |
| LYOPHILIZED *PLANTAGO LANCEOLATA* LEAVES EXTRACT | 0.8 |
| NATURAL STRAWBERRY FLAVOR, POWDER | 0.55 |
| NATURAL BLACKBERRY FLAVOR, POWDER | 0.5 |
| LYOPHILIZED *THYMUS VULGARIS* EXTRACT | 0.25 |
| XANTHAM GUM, POWDER | 0.2. |

12. The method of claim 6, wherein said composition consists of:

|  | % w/w |
|---|---|
| CANE SUGAR | 34 |
| HONEY | 31 |
| DEIONIZED WATER | 29 |
| *SAMBUCUS NIGRA* JUICE | 2.6 |
| LEMON JUICE | 0.7 |
| LYOPHILIZED *PLANTAGO LANCEOLATA* LEAVES EXTRACT | 0.9 |
| NATURAL STRAWBERRY FLAVOR, POWDER | 0.65 |
| NATURAL BLACKBERRY FLAVOR, POWDER | 0.5 |
| LYOPHILIZED *THYMUS VULGARIS* EXTRACT | 0.45 |
| XANTHAM GUM, POWDER | 0.2. |

13. The method of claim 8, wherein said composition consists of:

|  | % w/w |
|---|---|
| CANE SUGAR | 48 |
| HONEY | 30 |
| DEIONIZED WATER | 20 |
| LEMON JUICE | 0.6 |
| LYOPHILIZED *PLANTAGO LANCEOLATA* LEAVES EXTRACT | 0.58 |
| NATURAL ORANGE FLAVOR, POWDER | 0.2 |
| LYOPHILIZED *THYMUS VULGARIS*, EXTRACT | 0.3 |
| NATURAL STRAWBERRY FLAVOR, POWDER | 0.15 |
| NATURAL PEACH FLAVOR, POWDER | 0.10 |
| XANTHAM GUM, POWDER | 0.07. |

\* \* \* \* \*